(12) United States Patent
Neffgen et al.

(10) Patent No.: US 8,440,098 B2
(45) Date of Patent: May 14, 2013

(54) CONDITIONING AGENT FOR THE ETCHING OF ENAMEL LESIONS

(75) Inventors: Stephan Neffgen, Hamburg (DE); Swen Neander, Hamburg (DE); Dierk Lubbers, Halstenbek (DE)

(73) Assignee: Ernst Muhlbauer GmbH & Co. KG, Norderfriedrichskoog (DE)

( * ) Notice: Subject to any disclaimer, the term of this patent is extended or adjusted under 35 U.S.C. 154(b) by 567 days.

(21) Appl. No.: 12/422,063

(22) Filed: Apr. 10, 2009

(65) Prior Publication Data

US 2009/0256109 A1    Oct. 15, 2009

Related U.S. Application Data

(60) Provisional application No. 61/045,791, filed on Apr. 17, 2008.

(30) Foreign Application Priority Data

Apr. 11, 2008   (EP) .................................... 08007196

(51) Int. Cl.
    *C09K 13/04*      (2006.01)
(52) U.S. Cl.
    USPC .......... 252/79.4; 433/228.1; 424/49; 523/115
(58) Field of Classification Search ........................ None
    See application file for complete search history.

(56) References Cited

U.S. PATENT DOCUMENTS 6,312,667 B1 * 11/2001 Trom et al. ...................... 424/49
2003/0175218 A1 * 9/2003 Kanca, III ........................ 424/49
2006/0264532 A1 * 11/2006 Meyer-Luckel et al. ...... 523/115

FOREIGN PATENT DOCUMENTS

WO    2007131725 A1    11/2007

OTHER PUBLICATIONS

Serjeant et al, Ionization Constants of Organic Acids in Solution, 1979, Pergamon Press, p. 1-4.*
Bessler et al, Composition, Derwent -useful as an enzyme stabilizer in a liquid detergent for a cleaning agent, comprises an enzyme and an enzyme stabilizing componenet comprising a calcium compound with a bidentate ligand and a phynyl boric acid derivative, 2011, Derwent.*
Klocke A. et al., "An optimized synthetic substrate for orthodontic bond strength testing." 2003 Dental Materials 19 773.
Meyer-Lückel H. etal., "Surface Layer Erosion of Natural Caries Lesions with Phosphoric and Hydrochloric Acid Gels in Preparation for Resin Infiltration" 2007 Caries Research 41 223-230.

* cited by examiner

*Primary Examiner* — Nadine Norton
*Assistant Examiner* — David Cathey, Jr.
(74) *Attorney, Agent, or Firm* — Casimir Jones, S.C.

(57) ABSTRACT

The invention relates to a composition which comprises
  1 to 80% by weight of at least one acid which has a pKa of 2 or less;
  a protic solvent;
  a complexing agent for $Ca^{2+}$ ions;
  for use as conditioning agent for etching enamel lesions.

23 Claims, No Drawings

CONDITIONING AGENT FOR THE ETCHING OF ENAMEL LESIONS

The invention relates to a composition for use as conditioning agent for etching enamel lesions, and to a kit for infiltrating enamel lesions.

Caries is a widespread disease of civilization. Every incidence of caries which eventually leads to a cavity starts with demineralization of the dental enamel and, in this stage, is called initial enamel caries. In this stage, the caries is initially invisible or visible only as so-called white enamel lesion, but leads to a porous region of the tooth underneath its surface.

Such an enamel lesion can in principle be remineralized or infiltrated with a synthetic resin (WO 2007/131725 A1). However, a problem with the infiltration with synthetic resin is that a lesion which extends into the dental enamel typically has a so-called pseudointact surface layer on the tooth surface, which layer has a higher mineral content compared with the deeper enamel lesion and impedes or prevents penetration of the enamel lesion with the synthetic resin used for infiltration, called the infiltrant. It has therefore previously been proposed to pretreat these pseudointact surface layers by an etching agent so that, after this conditioning, the infiltrant can penetrate better into the lesion.

The invention is based on the object of providing an effective and readily storable and usable conditioning agent for etching enamel lesions.

The invention thus relates to a composition which comprises:
1 to 80% by weight of at least one acid which has a pKa of 2 or less;
a protic solvent;
a complexing agent for $Ca^{2+}$ ions;
for use as conditioning agent for etching enamel lesions.

The acid with a pKa of 2 or less may be an inorganic or organic acid, but mixtures of a plurality of acids are likewise possible. If the acid is polybasic, the first dissociation stage from the state of the acid present in the composition must have a pKa of 2 or less.

The protic solvent may be in particular alcohols or water or mixtures thereof.

The complexing agent for $Ca^{2+}$ ions may be any complexing agent which complexes, preferably substantially completely or to a considerable extent complexes, $Ca^{2+}$ ions dissolved out under the conditions of use of the composition in the oral environment.

The invention has recognized that the hydrochloric acid used in the prior art (WO 2007/131725 A1) as conditioning agent has a number of disadvantages. In order to be sufficiently effective as conditioning agent, approximately 15% strength hydrochloric acid must be used. HCl in more concentrated aqueous solutions has a considerable vapor pressure, so that it escapes in the form of a gas from the aqueous hydrochloric acid solution. Corresponding hydrochloric acid solutions thus have low storage stability; in addition, the resistance of the packaging of the conditioning agent is subject to great demands because the HCl escaping in the form of a gas is very aggressive. Furthermore, the HCl escaping in the form of a gas on use may damage biological tissues such as, for example, the gums.

The invention has recognized that the combination, defined in detail in the claim, of acids with a particular minimum acid strength and complexing agent can effectively erode, and thus prepare for the penetration of an infiltrant, the pseudointact surface layers of natural enamel lesions. Such pseudointact surface layers of a natural enamel lesion are typically 10 to 40 µm thick and are nevertheless substantially completely penetrated and removed by a composition of the invention in reasonable application times (for example about 90 to 120 s).

Surprisingly, the combination of an acid with an actually rather passive $Ca^{2+}$ ion complexing agent is able to etch the described remineralized surface layers sufficiently. This was not to be expected because complexation is actually suppressed by strong acids. It is additionally surprisingly possible according to the invention to reduce distinctly the concentration of the acid necessary to achieve an adequate etching effect. If volatile acids such as, for example, hydrochloric acid are used, this leads to aggressive acid constituents being evolved as gases during storage and use of the conditioning agents to only a very small extent or not at all.

The use of very strong acids with a pKa of 1 or less, more preferably of 0 or less, is preferred. For example, the pKa of the acid used may be between –10 and 1, and more preferably between –10 and 0.

The acid may be selected according to the invention from the group consisting of perchloric acid, hydrochloric acid, sulfuric acid, nitric acid, fluorosulfonic acid, organic sulfonic acids such as, for example, trifluoromethanesulfonic acid, methanesulfonic acid, toluenesulfonic acid, amidosulfonic acid, benzenesulfonic acid, trichloroacetic acid, trifluoroacetic acid, picric acid and semisquaric acid; more preferably selected from the group consisting of hydrochloric acid, nitric acid, methanesulfonic acid and toluenesulfonic acid. The acid content may be according to the invention preferably between 1 and 50% by weight, more preferably 4 and 30% by weight, more preferably 4 and 15% by weight.

A multidentate complexing agent, preferably a chelating agent, is preferably used according to the invention. It can be selected according to the invention from the group consisting of ethylenediaminetetraacetic acid (EDTA), diethylenetriaminepentaacetic acid (DTPA), nitrilotriacetic acid (NTA), iminodiacetic acid (IDA), glycolic acid, citric acid, 4-hydroxybutanoic acid, ethylenediaminetetra(methylenephosphonic acid) (DTPMP), diethylenetriaminepenta(methylenephosphonic acid) (EDTMP), aminotrismethylenephosphonic acid (ATMP), hydroxyethylaminodi(methylenephosphonic acid) (HEMPA), hexamethylenediaminetetra(methylenephosphonic acid) (HDTMP), phosphonobutane-1,2,4-tricarboxylic acid (PBTC), 1-hydroxyethane-1,1-diphosphonic acid (HEDP), polyacrylic acid and copolymers thereof and polyvinylphosphonic acid. A preferred lower limit for the content of complexing agents in the composition of the invention is 0.1% by weight, with more preferred lower limits being 1, 5 and 10% by weight. The complexing agent may be present in the composition up to the saturation limit, with preferred upper limits for the content of complexing agent being 80% by weight, 60% by weight and 40% by weight. The upper and lower limits mentioned can be combined as desired to give ranges according to the invention.

The complexing agents employed according to the invention preferably have a high affinity for divalent cations, in particular $Ca^{2+}$ ions. Good compatibility with the tissue of the mouth, especially gums, is preferred.

Complexing agents or in particular chelating agents can also be employed according to the invention in salt form. Salts of monovalent cations, for example the disodium salt of ETDA, are preferred.

The composition of the invention may additionally comprise thickeners such as, for example, particulate fillers or high-viscosity substances. Suitable thickeners are for example silicas, polyethers or polyols, and polyacrylic acids and copolymers thereof. Further additives such as, for example, colorants or surface-active substances (surfactants) may likewise be present.

The invention further relates to a kit for carrying out an infiltration of dental enamel which includes as constituents a conditioning composition of the invention, and an infiltrant. The infiltrant is preferably a curable (for example light-curable) synthetic resin which, after the preparation of the lesion by the conditioner, can penetrate into this lesion and seal it.

The infiltrant used in this kit preferably has a penetration coefficient of more than 50 cm/s. The penetration coefficient is calculated according to the equation which is detailed hereinafter and can be derived from the so-called Washburn equation:

$$PC = \left(\frac{\gamma \cdot \cos\theta}{2\eta}\right)$$

PC: penetration coefficient
γ: surface tension of the infiltrant at the air interface
θ: contact angle of the infiltrant at the enamel interface
η: dynamic viscosity of the infiltrant Further information on determination of the penetration coefficient, including literature references, are to be found in WO 2007/131725 A1, mentioned above, which is incorporated in the present disclosure by reference.

The infiltrant preferably comprises at least one resin selected from the group consisting of MMA, methyl methacrylate; EMA, ethyl methacrylate; n-BMA, n-butyl methacrylate; IBMA, isobutyl methacrylate, t-BMA, tert-butyl methacrylate; EHMA, 2-ethylhexyl methacrylate; LMA, lauryl methacrylate; TDMA, tridecyl methacrylate; SMA, stearyl methacrylate; CHMA, cyclohexyl methacrylate; BZMA, benzyl methacrylate; IBXMA, isobornyl methacrylate; MAA, methacrylic acid; HEMA, 2-hydroxyethyl methacrylate; HPMA, 2-hydroxypropyl methacrylate; DMMA, dimethylaminoethyl methacrylate; DEMA, diethylaminoethyl methacrylate; GMA, glycidyl methacrylate; THFMA, tetrahydrofurfuryl methacrylate; AMA, allyl methacrylate; EGDMA, ethylene glycol dimethacrylate; 3EGDMA, triethylene glycol dimethacrylate; 4EGDMA, tetraethylene glycol dimethacrylate; BDMA, 1,3-butylene glycol dimethacrylate; HDDMA, 1,6-hexanediol dimethacrylate; ETMA, ethoxyethyl methacrylate; 3FM, trifluoroethyl methacrylate; 8FM, octafluoropentyl methacrylate; AIB, isobutyl acrylate; TBA, tert-butyl acrylate; LA, lauryl acrylate; CEA, cetyl acrylate; STA, stearyl acrylate; CHA, cyclohexyl acrylate; BZA, benzyl acrylate; IBXA, isobornyl acrylate; 2-MTA, 2-methoxyethyl acrylate; ETA, 2-ethoxyethyl acrylate; EETA, ethoxyethoxyethyl acrylate; PEA, 2-phenoxyethyl acrylate; THFA, tetrahydrofurfuryl acrylate; HEA, 2-hydroxyethyl acrylate; HPA, 2-hydroxypropyl acrylate; 4HBA, 4-hydroxybutyl acrylate; DMA, dimethylaminoethyl acrylate; 1,4-butylenediol diacrylate; 4EDA, tetraethylene glycol diacrylate; NDDA, 1,9-nonanediol diacrylate; 3F, trifluoroethyl acrylate; 17F, heptadecafluorodecyl acrylate; 2-PEA, 2-phenoxyethyl acrylate; TBCH, 4-tert-butylcyclohexyl acrylate; DCPA, dihydrodicyclopentadienyl acrylate; EHA, 2-ethylhexyl acrylate; 3EGMA, triethylene glycol monomethacrylate; DEGDMA, diethylene glycol dimethacrylate; PDDMA, 1,5-pentanediol dimethacrylate; BDDMA, 1,4-butanediol dimethacrylate; PRDMA, 1,3-propanediol dimethacrylate (viscosity<30 mpas) or from the group consisting of DDDMA, 1,10-decanediol dimethacrylate; PEG400DA, polyethylene glycol 400 diacrylate, TMPTMA, trimethylolpropane trimethacrylate, TMPTA, trimethylolpropane triacrylate; DTMPTA; di-trimethylolpropane tetraacrylate; DiPENTA, di-pentaerythritol pentaacrylate; PEG400DMA, polyethylene glycol 400 dimethacrylate, PEG300DA, polyethylene glycol 300 diacrylate, PEG300DMA, polyethylene glycol 300 dimethacrylate, BPA(EO)10DMA, ethoxylated (10) bisphenol A dimethacrylate; BPA(EO)30DMA, ethoxylated (30) bisphenol A dimethacrylate; PEG200DA, polyethylene glycol 200 diacrylate, PEG600DA, polyethylene glycol 600 diacrylate; NPG(PO)2DA propoxylated (2) neopentyl glycol diacrylate; BPA(EO)2DA, ethoxylated (4) bisphenol A diacrylate; GPTA; propoxylated glyceryl triacrylate; DMTCDDA, dimethylol tricyclo[5.2.1.0$^{2,6}$]decane dimethacrylate; BPA(PO)2DMA, propoxylated (2) bisphenol A dimethacrylate; DPEHA, dipentaerythritol hexaacrylate; bis-GMA, 2,2-bis[4-(2-hydroxy-3-methacryloxypropoxy)phenyl]propane; and UDMA, 1,6-bis(methacryloxy-2-ethoxycarbonylamino)-2,4,4-trimethylhexane; (all the aforementioned resins have a viscosity>30 mpas).

Further preferred subgroups for the selection of the infiltrants are triethylene glycol dimethacrylate and trimethylolpropane trimethacrylate.

The kit of the invention may comprise application strips, cleaning strips and/or separators. The separator is an instrument with which a slight (for example about 300 µm) gap can be produced between the approximal surfaces of two adjacent teeth. Cleaning strips can be provided with an appropriate cleaning solution for preparative cleaning of dental surfaces to be treated. Application strips can be impregnated with the conditioning agent or the infiltrant and thus make it possible for these constituents of the kit to be applied simply and precisely even on the approximal surfaces, which are difficult to access, of teeth.

The suitability of various conditioning agents for eroding and demineralizing remineralized surface layers of natural enamel lesions is tested in a model system in the following exemplary embodiments and comparative examples.

These entailed investigating the etching effect on hydroxyapatite $[Ca_5(PO_4)_3OH]$ (hydroxyapatite disks) as model system for enamel, of which about 95% consists of hydroxyapatite. The etching effect of different conditioning agent or conditioner solutions can be estimated and classified therewith under reproducible conditions. The method is described in the publication by A. Klocke et al., Dental Materials 19 (2003), 773.

The hydroxyapatite disks were produced by hydraulic pressing (initial weight: 300 mg; pressure: 5000 bar; time: 35 min) of dried (2 h, 60° C.) hydroxyapatite (Riedel de Haen) with an IR press (from LOT GmbH). The disks were then embedded in a plastic (Paladur®, Heraeus Kulzer GmbH) in such a way that only one surface remained uncovered. This surface was processed with abrasive paper (500 and 1200 mesh) in order to obtain maximally reproducible surfaces, and was freed of abraded dust with compressed air. The diameter of the hydroxyapatite surface was 13 mm.

For the etching test, the hydroxyapatite disks were dipped in 4 ml of conditioner solution and shaken in a closed sample vessel on a shaker (GFL; 100 min$^{-1}$) for 2 min. The hydroxyapatite disks were then carefully removed from the solution with tweezers and thoroughly rinsed with water (hyperpure quality). The rinsing water was returned to the sample vessel. The contents of the sample vessel were then transferred into a 100 ml graduated flask, with the sample vessel being rinsed twice more with water, and the washing water likewise being collected in the graduated flask. The graduated flask was always made up to the 100 ml calibration mark with water. The Ca concentration in this solution was determined by atomic absorption spectroscopy (Perkin Elmer).

Table 1 below lists compositions of the invention as conditioning agents which were prepared by diluting commercially available acids and complexing agents in distilled water using a magnetic stirrer. Compositions 1 to 3 are comparative examples, and compositions 4 to 7 are examples of the invention. The last column of Table 1 indicates the calcium concentration obtained after the test described above for the respective acid. All percentage data are % by weight.

TABLE 1

| Acid [%] | pKa (pure acid) | Complexing agent [%] | Ca conc. [mg/l] |
|---|---|---|---|
| 1. Hydrochloric acid 1% | −7 | — | 4.9 |
| 2. Hydrochloric acid 5% | −7 | — | 17.7 |
| 3. Hydrochloric acid 15% | −7 | — | 20.35 |
| 4. Citric acid 60% | 3.1 | HEDP* 6% | 5.1 |
| 5. Hydrochloric acid 5% | −7 | HEDP 6% | 42.4 |
| 6. Hydrochloric acid 5% | −7 | HEDP 18% | 42.8 |
| 7. p-Toluenesulfonic acid 10% | −2 | HEDP 6% | 47.4 |

*1-Hydroxyethane-1,1-diphosphonic acid

The table shows that the compositions of the invention show a distinctly improved etching effect even compared with 15% strength hydrochloric acid, without showing the described disadvantages of hydrochloric acid.

Etching gels were produced from compositions 2, 3 and 5. For this purpose, the solutions were thickened by adding 5% by weight pyrogenic silica (Aerosil® 200, Degussa) and 0.5% by weight sorbitol-based polyetherpolyol with a hydroxyl value of 500. Mixing takes place in a Speedmixer (DAC 150 FV, from Hauschild).

Enamel samples were prepared from healthy caries-free human molars. The enamel surface was covered with nail varnish in such a way that uncovered enamel windows resulted. The etching gels to be tested were then applied to the enamel windows. After 120 s, the gels were removed with a jet of water. The samples were dried and embedded in Spurr's resin labeled with fluorescent dye (0.1 mM RITC). Examination took place with a confocal laser scanning microscope (CLSM) in fluorescence mode. A detailed description of the method is to be found in the publication of Meyer-Luckel H. et al., Surface layer erosion of natural caries lesions with phosphoric and hydrochloric acid gels in preparation for resin infiltration, caries research 2007, 41, 223-230.

| Gel | Action time [s] | Erosion depth [μm] |
|---|---|---|
| 15% HCl | 120 | 27.3 |
| 5% HCl | 120 | 13.3 |
| 5% HCl + 18% HEDP | 120 | 25.6 |

These examples and comparative examples show that a composition of the invention makes a large erosion depth possible without showing the described disadvantages of a highly concentrated hydrochloric acid solution. The indicated erosion depths are averages of 8 measurements.

The acids used in the exemplary embodiments do not, under the conditions of use, form insoluble calcium salts. This is generally a preferred feature of the invention.

The invention claimed is:

1. A kit for carrying out an infiltration of dental enamel, comprising:
   a) a conditioner comprising:
      i) 1 to 80% by weight of at least one acid which has a pKa of 2 or less;
      ii) a protic solvent;
      iii) a complexing agent for Ca2+ ions; and
   b) an infiltrant having a penetration coefficient PC of >50 cm/s.

2. The kit as claimed in claim 1, wherein the infiltrant comprises at least one resin selected from the group consisting of MMA, methyl methacrylate; EMA, ethyl methacrylate; n-BMA, n-butyl methacrylate; IBMA, isobutyl methacrylate, t-BMA, tert-butyl methacrylate; EHMA, 2-ethylhexyl methacrylate; LMA, lauryl methacrylate; TDMA, tridecyl methacrylate; SMA, stearyl methacrylate; CHMA, cyclohexyl methacrylate; BZMA, benzyl methacrylate; IBXMA, isobornyl methacrylate; MAA, methacrylic acid; HEMA, 2-hydroxyethyl methacrylate; HPMA, 2-hydroxypropyl methacrylate; DMMA, dimethylaminoethyl methacrylate; DEMA, diethylaminoethyl methacrylate; GMA, glycidyl methacrylate; THFMA, tetrahydrofurfuryl methacrylate; AMA, allyl methacrylate; EGDMA, ethylene glycol dimethacrylate; 3EGDMA, triethylene glycol dimethacrylate; 4EGDMA, tetraethylene glycol dimethacrylate; BDMA, 1,3-butylene glycol dimethacrylate; HDDMA, 1,6-hexanediol dimethacrylate; ETMA, ethoxyethyl methacrylate; 3FM, trifluoroethyl methacrylate; 8FM, octafluoropentyl methacrylate; AIB, isobutyl acrylate; TBA, tert-butyl acrylate; LA, lauryl acrylate; CEA, cetyl acrylate; STA, stearyl acrylate; CHA, cyclohexyl acrylate; BZA, benzyl acrylate; IBXA, isobornyl acrylate; 2-MTA, 2-methoxyethyl acrylate; ETA, 2-ethoxyethyl acrylate; EETA, ethoxyethoxyethyl acrylate; PEA, 2-phenoxyethyl acrylate; THFA, tetrahydrofurfuryl acrylate; HEA, 2-hydroxyethyl acrylate; HPA, 2-hydroxypropyl acrylate; 4HBA, 4-hydroxybutyl acrylate; DMA, dimethylaminoethyl acrylate; 1,4-butylenediol diacrylate; 4EDA, tetraethylene glycol diacrylate; NDDA, 1,9-nonanediol diacrylate; 3F, trifluoroethyl acrylate; 17F, heptadecafluorodecyl acrylate; 2-PEA, 2-phenoxyethyl acrylate; TBCH, 4-tert-butylcyclohexyl acrylate; DCPA, dihydrodicyclopentadienyl acrylate; EHA, 2-ethylhexyl acrylate; 3EGMA, triethylene glycol monomethacrylate; DEGDMA, diethylene glycol dimethacrylate; PDDMA, 1,5-pentanediol dimethacrylate; BDDMA, 1,4-butanediol dimethacrylate; PRDMA, 1,3-propanediol dimethacrylate; DDDMA, 1,10-decanediol dimethacrylate; PEG400DA, polyethylene glycol 400 diacrylate, TMPTMA, trimethylolpropane trimethacrylate, TMPTA, trimethylolpropane triacrylate; DTMPTA; di-trimethylolpropane tetraacrylate; DiPENTA, di-pentaerythritol pentaacrylate; PEG400DMA, polyethylene glycol 400 dimethacrylate, PEG300DA, polyethylene glycol 300 diacrylate, PEG300DMA, polyethylene glycol 300 dimethacrylate, BPA(EO)10DMA, ethoxylated (10) bisphenol A dimethacrylate; BPA(EO)30DMA, ethoxylated (30) bisphenol A dimethacrylate; PEG200DA, polyethylene glycol 200 diacrylate, PEG600DA, polyethylene glycol 600 diacrylate; NPG(PO)2DA propoxylated (2) neopentyl glycol diacrylate; BPA(EO)2DA, ethoxylated (4) bisphenol A diacrylate; GPTA; propoxylated glyceryl triacrylate; DMTCDDA, dimethylol tricyclo[5.2.1.02,6]decane dimethacrylate; BPA(PO)2DMA, propoxylated (2) bisphenol A dimethacrylate; DPEHA, dipentaerythritol hexaacrylate; bis-GMA, 2,2-bis[4-(2-hydroxy-3-methacryloxypropoxy)phenyl]propane; and UDMA, 1,6-bis(methacryloxy-2-ethoxycarbonylamino)-2,4,4-trimethylhexane.

3. The kit as claimed in claim 1, wherein the infiltrant comprises at least one resin selected from the group consisting of polymethacrylic acids and derivatives thereof.

4. The kit as claimed in claim 1, which comprises at least one application strip and/or cleaning strip and/or a separator.

5. The kit as claimed in claim 4, which comprises an application strip provided with a conditioner.

6. The kit as claimed in claim 4, which comprises an application strip provided with an infiltrant.

7. The kit as claimed in claim 1, wherein the infiltrant comprises at least one resin selected from the group consisting of 3EGDMA, triethylene glycol dimethacrylate; and TMPTMA, trimethylolpropane trimethacrylate.

8. The kit as claimed in claim 1, wherein the acid content of said conditioner is from 1 to 50% by weight.

9. The kit as claimed in claim 1, wherein the acid content of said conditioner is 4 to 30% by weight.

10. The kit as claimed in claim 1, wherein the acid content of said conditioner is 4 to 15% by weight.

11. The kit as claimed in claim 1, wherein the pKa of the acid in said conditioner is from −10 to 1.

12. The kit as claimed in claim 1, wherein the pKa of the acid in said conditioner is from −10 to 0.

13. The kit as claimed in claim 1, wherein the acid in said conditioner is selected from the group consisting of perchloric acid, hydrochloric acid, sulfuric acid, nitric acid, fluorosulfonic acid, trifluoromethanesulfonic acid, methanesulfonic acid, toluenesulfonic acid, trichloroacetic acid, trifluoroacetic acid, picric acid and semisquaric acid.

14. The kit as claimed in claim 1, wherein the acid in said conditioner is selected from the group consisting of hydrochloric acid, nitric acid, methanesulfonic acid and toluenesulfonic acid.

15. The kit as claimed in claim 1, wherein the complexing agent in said conditioner is multidentate.

16. The kit as claimed in claim 1, wherein the complexing agent in said conditioner is a chelating agent.

17. The kit as claimed in claim 16, wherein the chelating agent is selected from the group consisting of ethylenediaminetetraacetic acid (EDTA), diethylenetriaminepentaacetic acid (DTPA), nitrilotriacetic acid (NTA), iminodiacetic acid (IDA), glycolic acid, 4-hydroxybutanoic acid, ethylenediaminetetra(methylenephosphonic acid) (DTPMP), diethylenetriaminepenta-(methylene-phosphonic acid) (EDTMP), aminotrismethylene-phosphonic acid (ATMP), hydroxyethylaminodi-(methylenephosphonic acid) (HEMPA), hexamethylene-diaminetetra(methylenephosphonic acid) (HDTMP), phosphonobutane-1,2,4-tricarboxylic acid (PBTC), and 1-hydroxyethane-1,1-diphosphonic acid (HEDP).

18. The kit as claimed in claim 1, wherein the complexing agent content in said conditioner is from 0.1 to 80% by weight.

19. The kit as claimed in claim 18, wherein the complexing agent content in said conditioner is from 1 to 80% by weight.

20. The kit as claimed in claim 19, wherein the complexing agent content in said conditioner is from 5 to 60% by weight.

21. The kit as claimed in claim 20, wherein the complexing agent content in said conditioner is from 10 to 40% by weight.

22. The kit as claimed in claim 1, wherein the, wherein said conditioner additionally comprises at least one thickener.

23. The kit as claimed in claim 22, wherein the at least one thickener is selected from the group consisting of particulate fillers and polyethers.

* * * * *